United States Patent [19]
Brennan et al.

[11] Patent Number: 5,681,975
[45] Date of Patent: Oct. 28, 1997

[54] SINGLE SOURCE METALLOORGRANIC PRECURSORS TO TYPE 14-16 SEMICONDUCTORS

[75] Inventors: John Brennan, Highland Park; Yifeng Cheng, Edison, both of N.J.

[73] Assignee: Rutgers, The State University, New Brunswick, N.J.

[21] Appl. No.: 563,631

[22] Filed: Nov. 28, 1995

Related U.S. Application Data

[63] Continuation-in-part of Ser. No. 275,618, Jul. 14, 1994, Pat. No. 5,527,909.

[51] Int. Cl.$^6$ .............................. C07F 7/00; C22C 11/00; C22C 13/00; C22C 28/00
[52] U.S. Cl. ........................ 556/81; 544/64; 546/2; 546/153; 548/403; 420/556; 420/557; 420/563
[58] Field of Search ........................... 544/64; 546/2, 546/153; 548/403; 556/12, 20, 81; 420/556, 557, 563

[56] References Cited

FOREIGN PATENT DOCUMENTS 2703873  8/1977  Germany .
1298010  12/1989  Japan .

OTHER PUBLICATIONS

Stephan R. Bahr et al., Chemistry Materials, vol. 4, pp. 383–388 (1992).
Allen L. Seligson et al., Journal of American Chemistry Society, vol. 115, pp. 8214–8220, (1993).
Gertruck Krauter et al., Materials Research Society Symposium Proceedings, vol. 327, pp. 41–46, (1994).
Phillip Bordjock et al., Chemistry Materials, vol. 4, pp. 383–388 1994; vol. 6 pp. 2108–2112 (1994).
H. M. Manasevit et al, J. Electrocehm. Soc., vol. 122, p. 444 (1975).
Phillip Bondjouk et al., Chemistry Materials, vol. 4, pp. 383–388 (1992).
Domazetis et al., J. Inorg. Nucl. Chem., vol. 43, pp. 1351–1359 (1981).
Domazetis et al., J. Inorg. Nucl. Chem., vol. 41, pp. 1555–1562 (1979).
Talley et al., J. Organomet. Chem., vol. 215, pp. c38–c40 (1981).

*Primary Examiner*—Porfirio Nazario-Gonzalez
*Attorney, Agent, or Firm*—John F. Ritter

[57] ABSTRACT

The present invention relates to a single source metalloorganic precursor compound of the formula:

$$(2\text{-NR-Q-})_l M\text{-}A_m \quad (l=0\text{-}4,\ m=0\text{-}4,\ l+m=2\ or\ 4)$$

wherein M is selected form the Group 14 elements of Germanium, Tin or Lead;

A and R are independently selected from: amide, alkyl having from 1 to 20 carbon atoms, aryl, substituted aryl, or -Q'-2-NR'L$_n$ (n=1–4) wherein L is selected from nothing or a Lewis base ligand;

Q and Q' are each independently selected from Group VIa elements of sulfur, selenium, or tellurium; and 2-NR and 2-NR' are each independently selected from N-heterocyclic aryl or its derivatives.

Methods of producing these compounds are also disclosed. These precursor materials provide in a single compound the binary, tertiary, or quaternary metals in a ratio to each other that is controllable by a judicious choice of metal atoms and organic substituents. The metal alloys are useful in a variety for electronic applications, particularly in semiconductors and solar energy.

16 Claims, No Drawings

SINGLE SOURCE METALLOORGRANIC PRECURSORS TO TYPE 14-16 SEMICONDUCTORS

CROSS REFERENCE TO RELATED APPLICATIONS

This invention is a continuation-in-part of U.S. application Ser. No. 08/275,618 filed on Jul. 14, 1994 now U.S. Pat. No. 5,527,909 by John G. Brennan and Yifeng Cheng.

This invention was made with Government Support under the National Science Foundation, Grant No. CHE 9204160, and as such the Government has certain rights to this invention.

BACKGROUND OF THE INVENTION

A. Field of the Invention

The present invention relates to the preparation of novel metal organic precursor compounds comprising at least one metal from Group 14 and at least one element from Group 16 of the Periodic Table. More specifically, these novel 14/16 compounds are useful as single source metalloorganic tellurium, selenium, sulfur, germanium, tin or lead containing precursors in the preparation of semiconducting materials having precisely defined elemental ratios.

B. Description of the Related Art

Group 14/16 semiconducting thin-film alloys are becoming increasingly important due to their useful electrical properties. The 14/16 alloys are useful in a wide range of applications including, but not limited to, solar cells, photovoltaic cells, infrared sensors and lasers, polarized lasers, thermoelectric cooling devices, and optical information recording mediums. The following are some examples of the use of 14/16 semiconductors in a variety of different applications:

(1) SnS, SnSe, GeS and GeSe, used in optoelectronics, holographic recording systems, electrical switching, and solar cells (SnSe [1 eV bandgap]). SnS (1.3 eV) is especially favorable in such applications due to its high conversion efficiency in photovoltaic devices (25%). Moreover, SnTe is used as a narrow bandgap semiconductor (0.33 eV) in a variety of infrared detectors;

(2) $Pb_{1-x}Sn_xTe$, used in the fabrication of photovoltaic detectors and diode lasers operating in the 8–14 micron atmospheric window;

(3) PbS, which has a high response in the near-IR region (13 microns), used in photoconducting detectors, spectrometric sensors, flame monitors, missile guidance systems, and numerous other devices; and (4) $PbSe_{1-x}Te_x$, deposited on Group IIA fluoride insulators, have recently shown great promise as novel large focal-plane-array thermal-imaging devices. This represents perhaps the greatest degree of optoelectronic integration ever achieved on a silicon substrate.

A major advantage of 14–16 semiconductors over other narrow gap semiconductors such as 12–16 materials (i.e CdSe), is the relative ease in which both n-type and p-type materials can be grown. This allows fabrication of advanced device structures such as injection lasers in addition to simple Schottky barrier device structures. Moreover, materials causing point defects in 14–16 semiconductors are not as prominent as in other semiconductors because of the large dielectric screening (the static dielectric constants of PbSe and PbTe are 206 and 380, respectively). The 14–16 semiconductors are therefore relatively "forgiving" materials for device fabrication and thus an attractive alternative to other semiconductors, such as 12/16 compounds.

Group 14/16 semiconductors can be obtained in thin film form by evaporation, pyrolysis and chemical deposition techniques, all of which are currently used in industry. However, the optical and electrical characteristics of the deposited materials are often heavily dependent on the deposition technique. Chemical solution growth is simple, relatively inexpensive, and convenient for large area deposition of 14/16 compounds. However, the final semiconductor films often contain a stoichiometric excess of Group VIa elements as well as water and have to be annealed at high temperatures to remove these impurities.

Both vapor phase epitaxy (VPE) and liquid phase epitaxy (LPE) deposition techniques do not hold promise for controlling the desired stoichiometry. Furthermore, due to the relatively high temperature of the process, there is sufficient group 14 metal and chalogen atom inter-diffusion which introduces a composition gradient at the interface. Such gradients will negatively impact the quality of the semiconductors.

An alternative processing technique involves organometallic chemical vapor deposition ("OMCVD"). OMCVD has been used extensively for many types of semiconductor materials. Recently, PbS thin films have been prepared by atomic layer epitaxy using $H_2S$ and certain lead salts (e.g lead bromide, lead iodide, lead beta-diketonate, and lead alkoxides compounds) as starting materials. However, each of these routes demands a vigorous high temperature pyrolysis to give pure PbS. The photoconductive properties, mainly carrier concentration and lifetime, are affected by the stoichiometry of the films and their doping (by halogen, oxygen, etc).

Tin and lead chalcogenides have been prepared using OMCVD in which tetraalkyl group 14 compounds and $H_2S$, $H_2Se$ or $Me_2Te$ were combined in a OMCVD reactor (at 625° C. for $Me_4Sn$ with $H_2S$) to produce tin and lead chalcogenide thin films. (See Manasevit, H. M; Simpson, W. I., J. Electochem. Soc. 1975, Vol. 122, pp 444). The disadvantages of using this technique include the high volatility and high toxicity associated with the starting materials and a tedious purification process. Moreover, effective mixing of the compounds in the gas phase is difficult to ensure.

Many of the disadvantages of the aforementioned techniques can be alleviated with the use of single-source precursors in which the elements desired in the final semiconductor are incorporated in one molecule. Typically, the precursor molecules have higher molecular weights and lower vapor pressures, thus making the materials safer to handle. The ease with which these compounds can be weighed, transferred, and mixed, eliminates the need for elaborate vacuum line setups and sophisticated valving systems. Furthermore, the practitioner has greater stoichiometric control when using single-source precursors.

Other advantages that single-source processing offers is the possible fabrication of unusual phases of solid state materials, the achievement of site-selective doping of semiconducting materials, and unexpected growth morphologies for the final materials. While in recent years the single-source precursor method had been explored extensively for 13–15 and 12–16 semiconductors, single-source precursors leading to 14–16 compounds have been studied far less extensively.

Metal chalcogenolates possess the potential to serve as single-source precursors for metal chalcogenides. However, due to their polymeric nature, purification by recrystallization is extremely difficult and often impossible. Two approaches can be envisioned to overcome these difficulties.

one of which involves the choice of bulky organic groups to encourage the formation of compounds with a relatively low degree of molecular association. Unfortunately, bulky organic groups increase the tendency of metals to undergo reducvitive elimination and form elemental metals rather than metal chalcogens. Furthermore, the complicated ligand systems may decompose to form many by-products that may be harmful to the reactor and the final semiconductor films.

The other approach to preparing soluble, readily crystallized, metal chalcogenolates uses Lewis bases to form coordination complexes and chemically disrupt the polymeric lattice. However, because of the weak bond between the Lewis bases and metal center, Lewis bases have shown a tendency to dissociate at reduced temperatures, leaving behind involatile polymeric materials. This ligand dissociation process renders these materials virtually useless in metalloorganic chemical vapor deposition (MOCVD) processes.

Some general reports of the production of 14–16 materials using separated metalloorganic compounds include, for example:

Domrachev, G. A; Khamylov, V. K Bochkarev, M. N.; Zhuk, B. V; Kaverin, B. S; Nesterov, B. A; Kirilov, A. I; German Patent 2,703,873 (1977), describes the pyrolysis of compounds of the type $R_kE_lX_mR_n(R,R'=C_{1-4}$ alkyl group; E=group 14; X=group 16; k=0–6; l=1–2; m=1–4; n=0–4) to give composite metal sulfides and selenides.

Uchida, H., Japanese Patent 01,298,010 (1989), reports the pyrolysis of metal selenolates, $\{R_2NC(Z)Se\}_nM^{n+}$ or $\{ROC(Z)Se\}_nM^{n+}$ (R=$C_{1-10}$ alkyl group; M=metals; Z=O, Se; n=1–5) at 250°–450° C. to give metal selenides useful for semiconductor devices and solar cells.

Steven R. Bahr et al. (1992) Chemistry Materials, Vol. 4 pp383–388, reports that group 14–16 six-membered ring systems of the general formula $(Ph_2SnX)_3$ (X=S and Se) serve as convenient single-source precursors to microcrystalline powders of SnS and SnSe under very mild conditions.

Allen L. Seligson and John Arnold (1993) Journal of American Chemistry Society, vol. 115, pp 8214–8220, describes the preparation and characterization of homoleptic tin (II) and lead (II)tellurolates, selenolates, and thiolates incorporating bulky [ESi(SiMe$_3$)$_3$] ligands (E=Te, Se, or S) and pyrolysis of these compounds to give ME semiconductors.

Gertrude Krauter et al (1994) Materials Research Society Symposium Proceedings, Vol. 327, pp 41–46, describes preparation and characterization of Group 14 element Bis (thiolate) compounds and evaluation of their potential as molecular precursors in the low temperature syntheses of binary metal sulfides.

Philip Boudjouk et al (1994) Chemistry Materials, Vol. 6, pp 2108–2112, presents the results of the pyrolysis study of linear compounds, $(Ph_3Sn)_2X$, (X=S, Se and Te), which serve as convenient single-source precursors to microcrystalline powders of SnS, SnSe and SnTe.

Phillip Bondjouk et al. reported that Group 14–16 six membered ring system of the general formula $(Ph_2SnX)_3$ (X=S and Se) and Bis(triphenyltin) chalcogenide serve as convenient single-source precursors to microcrystalline powders of SnS and SnSe. Chemistry Materials, 1992, Vol. 4, pp 383–388 and 1994, Vol. 6, pp 2108–2112. However, these phenyl-substituted systems have a very high molecular weight, a very low vapor pressure, and a complicated complex and therefore gives carbon residue in the final semiconductors.

The present invention improves on all known CVD precursors, as well as the involatile materials of Bondjouk and Arnold, by covalently binding a strong neutral donor atom to the chalcogenolate functional group. This enhances compound volatility by minimizing polymer formation in the solid state, saturating the metal coordination sphere in the vapor phase, and stabilizing gas phase species. Furthermore, the small size of the organic substituent minimizes many of the problems associated with competing processes.

Importantly, the present invention, unlike the compounds of Bondjouk and Arnold, drastically reduces the possibility of incorporating carbon and hydrogen impurities and elemental Pb or Sn in the final solid state product. In the present invention, there is only one viable decomposition pathway because there is only one weak bond (CE,E=S, Se,Te) being ruptured.

All of the references, patents, standards, etc. referenced in this application are incorporated herein by reference.

The problems in this art remain, i.e the reactive precursors, undesirable pre-reactions, side reactions and non or low volatility. It would be extremely useful to have the metals of interest in a single, stable and volatile metalloorganic precursor compound so that the metals or chalcogens can be precisely controlled. The present invention provides such precursor compounds and process to produce them.

SUMMARY OF THE INVENTION

It is an object of the present invention to provide a single-source metalloorganic precursor.

It is another object of the present invention to provide a metalloorganic precursor which is structurally simple so as to evolve stable organic by-products which do not react further to contaminate the final product.

It is yet another object of the present invention to provide a metalloorganic precursor capable of depositing the metals of interest in precise ratios.

The present invention relates to a metal organic compound of the formula:

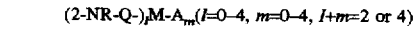

$(2\text{-NR-Q-})_l\text{M-A}_m (l=0\text{–}4, m=0\text{–}4, l+m=2 \text{ or } 4)$ Wherein M is selected from the Group 14 elements of Germanium, Tin and Lead;

A is selected from an amide, alkyl having from 1 to 20 carbon atoms, aryl, substituted aryl group, or -Q'-2-NR'L$_n$ (n=1–4) wherein L is selected from nothing or a Lewis based ligand;

Q and Q' are each independently selected from Group 16 elements of sulfur, selenium, or tellurium; and 2-NR and 2-NR' are each independently selected from N-heterocyclic aryl or its derivatives.

Preferably, the metal compound has A as -Q'-2-NR and L is nothing, especially wherein 2-NR=2-NR', and Q=Q'.

In one embodiment, Q is selenium, primarily wherein M is germanium, tin or lead.

In a preferred embodiment, the metal compound has 2-NR' as pyridinyl or 3-TMS-2-pyridinyl, more preferably, wherein Q and Q' are selenium.

In another embodiment, the metal compound has L as the Lewis base ligand which is independently selected from pyridine, substituted pyridine, pyrrole, substituted pyrrole, quinoline, morphine, 2,2'-bipyridyl organic phosphine, organic arsine, alkyl ether, aryl ether, thioether, amine, chelate of diamines, diphosphines, diarsines, diethers or mixtures thereof.

In another embodiment, the present invention also concerns a process for the production of a metal organic compound of the formula:

(2-NR-$Q$-)$_l$$M$-$A$=($l$=0–4, $m$=0–4, $l$+$m$=2 or 4)

Wherein M is selected from the Group 14 elements of Germanium, Tin and Lead;

A is selected from: an amide, alkyl having from 1 to 20 carbon atoms, aryl substituted aryl group, or -Q'-2-NR'-L$_n$ (n=1–4) wherein L is selected from nothing or a Lewis base ligand, Q and Q' are each independently selected from Group 16 elements of sulfur, selenium, or tellurium; and 2-NR and 2-NR' are each independently selected from N-heterocyclic aryl or its derivatives which process comprises:

(A) contacting L'$_n$-Z-2-NR (n=1–4) wherein L' is independently selected from ligand L, Z is independently selected from lithium, sodium, potassium, magnesium, calcium, barium, or strontium; and 2-NR is as defined hereinabove, with a metal powder Q wherein Q is defined herein above, in a polar solvent under an inert anhydrous atmosphere for between about 0.01 and 2 hours between –20° and +30° C. to give Z-Q-2-NR' L$_n$';

(B) contacting the product of step (A) with a strong or a weak acid, and removing the polar solvent to give

H-Q-2-NR wherein Q and 2-NR are defined hereinabove;

(C) contacting the product of step (B) with:

(1)MX$_n$(n=2 or 4) salt in a n:1 ratio in organic solvent at between about –20° and +50° C., and for between about 0.01 and 2 hours, or (2)MR$_n$ (n=2 or 4) in a n:1 ratio in an a polar solvent at between about –20° and +30° C., and for between about 0.01 and 2 hours, or (3)M(R')$_n$ or MX$_n$ (n=2 or 4) wherein R' is independently selected from R and R is defined as an alkyl, aryl, substituted aryl, amino beta-diketonate, in any ratio in a polar solvent at between –20° and +100° C. and for between about 0.01 and 2 hours, followed by treatment with one H-Q'-2-NR', where Q' and 2-NR' are defined above, in a polar solvent at between –20° and +100° C. and for between about 0.01 and 2 hours;

(D) recovering the metalloorganic compound of structure (I), where L is nothing; and (E) optionally contacting the product of step (D) with ligand L to produce an organometallic compound where L is a Lewis base.

in another aspect, the present invention relates to a process for the production of a binary, ternary or quaternary metal alloy, which process comprises:

(F) subjecting the metalloorganic compound of step (D) or (E) above to a temperature of between about 100° C. and 500° C, in an anhydrous vacuum or inert atmosphere at ambient pressure (e.g. $10^{-2}$ to $10^{-6}$ Torr), especially the metal alloy producing process wherein A is -Q'2-NR', and Q=Q', and 2-NR=2-NR'.

DETAILED DESCRIPTION Of PREFERRED EMBODIMENTS

1. DEFINITIONS

As used herein:

"Alkyl" refers to all alkyl groups usually having 1 to 20 carbon atoms including, but not limited to, straight chain, branched, and 4, 5, or 6 member hydrocarbon rings. "Aryl" refers to phenyl, naphthylene, anthracene, phenathrene and other aromatic hydrocarbon groups. Aryl also includes groups such as —C(phenyl)$_3$, —C(4-methylphenyl)$_3$, —C(4-methoxyphenyl)$_3$ and the like. Moreover, Aryl also includes heterocyclic aryl groups such as pyridine, pyrrole, quinoline, furan and the like. Hydrocarbons such as phenyl are preferred. "X" refers to halogen, nitrate, organic acid and the like. "Substituted aryl" refers to alkyl (C$_{1-20}$) or halogen substituted for one or more protons one the aryl ring. Generally 0, 1, 2, or 3 proton substitutes are preferred. Substituted aryl also includes substituted heterocyclic aryl groups. "N-heterocyclic aryl" refers to pyridine, pyrrole, quinoline and the like. "Substituted N-heterocyclic aryl" refers to silyl, alkyl (C$_{1-20}$), halogen, amine, amide, nitro and the like substituted for one or more protons on the aryl ring. Generally 1, 2 or 3 proton substitutions are preferred. "Silyl" refers to —SiR$_1$R$_2$R$_3$ groups, where R$_i$(i=1, 2 or 3) are alkyl, aryl, X substituted aryl, N-heterocyclic aryl, or substituted N-heterocyclic aryl.

2. GENERAL SYNTHESIS

A typical experiment is described to produce a symmetric (with reference to the M atom) metalloorganic compound. First, 2-NR-X and ZHQ or Z$_2$Q in a n:1 (n=0.1–10.0) molar ratio are combined, stirred, and heated in an anhydrous aprotic polar solvent, such as dimethylformamide (DMF), dimethylsulfoxide (DMSO), hexamethylphosphoramide (HMPA) or the like, or an anhydrous protic polar solvent, such as alcohols or the like under a stream of nitrogen at between about 20° C. to 35° C. for between about 5 minutes and one week. The corresponding 2-NR-Q-Q-2-NR or H-Q-2-NR is produced in good yield. When H-Q-2NR is treated with air or oxygen in water or organic solvent, good yields of the corresponding 2-NR-Q-Q-2-NR are also obtained. When 2-NR-Q-Q-2-NR is treated with reducing reagents in anhydrous polar solvents, the corresponding L$_n$Z-Q-2-NR (n=1–4) is obtained in almost quantitative yield with the addition of ligand L reagents.

Z is independently selected from alkali metals. Sodium is preferred.

Q is independently selected from sulfur, selenium or tellurium. Selenium is preferred.

L is the Lewis base ligand which is independently selected from pyridine, substituted pyridine, pyrrole, substituted pyrrole, quinoline, morphine, 2,2'bipyridyl, organic phosphine, organic arsine, alkyl ether, aryl ether, thioether, amine, chelates of diamines, diphosphines, diarsines, diethers or mixtures thereof.

The substituted N-heterocyclic aryl-Q-H or di substituted N-heterocyclic aryl dichalcogenide can be prepared as follows: (1) 2-NR-Q-H is contacted with 2 or more equivalent of lithiation reagents (n-butyllithium-N,N,N',N'-tetramethylethylenediamine (TMEDA), lithium diisopropylamide (LDA), etc) in anhydrous organic solvent under anhydrous inert atmosphere at between –10° and –78° C. for about between 0.01 and 36 hours and then contacted with 2 eq or excess substituted group X (X is halogen) under an anhydrous inert atmosphere at between 0° and –78° C. for between 0.01 and 36 hours and then warming to room temperature for between about 0.01 hour and one week.

Alternative (2), 2-NR-Q-Li is contacted with 1 or more equivalents of lithiation reagents (n-butyllithium-N,N,N',N'-tetramethylethylenediamine(TMEDA), lithium diisopropylamide (LDA), etc.), in an anhydrous organic solvent under anhydrous inert atmosphere at between –10° and –78° C. for between 0.01 and 36 hours and then contacted with 1 or more equivalents of substituted group X (wherein X is a halogen) under anhydrous inert atmosphere at between 0° and 78° C. for between 0.01 and 36 hours and then warming to room temperature for between about 0.01 hour and one week.

The compound M(-Q-2-NR)$_n$ can be prepared by several routes, as follows:

(1) 2-NP-Q-H is contacted with MX$_n$-L$_m$ (m=0–4) (n=2 or 4) (X is halogen, SiF$_6^{2-}$, BF$_4^-$-alkoxyl) in a n:1 equivalent ratio in polar solvent with or without some Lewis base at between −20° C. and +100° C. for between 0.01 and 12 hours.

Alternative (2). Z-Q-2-NR is contacted with MX$_n$L$_m$ (n=0–4) in a n:1 equivalent ratio in polar solvent or water at between −200° and +100° C. for between about 0.01 and 12 hours.

Alternative (3). 2-NR-Q-Q-2-NR is contacted with metal M in a (n/2):1 (n=2 or 4) equivalent ratio in anhydrous polar solvent under an anhydrous inert atmosphere at between −20° C. and +250° C. for between about 0.1 hour and one week.

Alternative (4). 2-NR-Q-H is contacted with M(R)$_n$ (n=2 or 4) in a n:1 ratio in an polar solvent at between about −20° C. and 100° C. (preferably ambient temperature) for between about 0.01 and 3 hours.

Alternative (5). (2-NR-Q-)$_l$-MR"$_m$ (R is alkyl,aryl, substituted aryl, or amino beta-diketonate) (l=0–4, m=0–4, l+m=2 or 4) (1 eq) is contacted with 2-NR'-Q'-H in a 1:m ratio in a polar solvent at between about −20° C. and 100° C. (preferably ambient temperature) for between about 0.01 and 3 hour.

Alternative (6). (2-NR-Q-)$_l$M-X$_m$ (l=0–4, m=0–4, l+m=2 or 4) is contacted with H-Q'-2-NR' in a polar solvent or water with or without some Lewis base at between about 20° C. and 100° C. (preferably ambient temperature) for between about 0.01 and 3 hours.

To obtain a binary alloy, M and Q are as defined hereinabove for alternative 1, 2 or 3. To obtain a ternary alloy, M and Q are as defined hereinabove and Q' is present and is different from Q in alternative (5, 6) above. To obtain ternary or quaternary (or higher) alloys, it is possible to physically combine the compounds produced in alternatives 1, 2, 3, 4, 5, or 6 above in a hot polar solvent and recovering the mixed solid compounds upon cooling.

The metalloorganic compounds of the present invention are dimeric, trimeric, or quasi-1D polymeric with weakly connected units and exist as monomers in the gas phase. For this reason, they have the volatility necessary to be transferred within reaction lines and vessels under conventional inert atmospheric conditions. These properties are in stark contrast with those metalloorganic compounds of the art which have a higher degree of polymerization, or larger molecular and organometallic compounds which am essentially non-volatile.

3. EXPERIMENTAL METHOD USED FOR GROWTH OF 14/16 FILMS

Any of the precursor materials are deposited on to substrates such as quartz or GaAs in the following manner. A quartz tube containing the precursor compound and a slice or wafer of the substrate material is placed inside a resistively heated tube furnace having a temperature gradient ranging from 100° C. to 600° C. along the length of the apparatus. The compound is placed at the cooler end of the tube while a steam of nitrogen or argon gas is passed through over the compound and toward the substrate. On impinging the hot substrate, the precursor compound decomposes, depositing a thin film of 14–16 alloy. The volatile decomposition products are removed in the gas stream.

Alternatively, the above process can be carried out under high vacuum (10$^{-2}$ to 10$^{-6}$ Torr) using the vapor pressure of the gaseous compound to transport the material to the substrate. In this case, the decomposition products condense in a part of the tube held at a much lower temperature (15°–45° C.).

4. PYROLYSIS OF METALLOORGANIC COMPOUNDS

The pyrolysis of the compounds by conventional means in the art is contemplated. For example, pyrolysis of Sn(SePy)$_2$ proceeds as in the following equation:

Thus, exactly 50% of the selenium in the starting materials is converted to metal selenide. The remaining 50% of the selenium is removed from the system as stable, volatile Py-Se-Py.

5. GENERAL

The chemical agents, reagents and solvents described above are usually used as obtained from US chemical supply plants, e.g Aldrich Chemical Co. All syntheses were carried out under ultra pure nitrogen (JWS), using conventional drybox or Schlenk Techniques. Melting points were taken in sealed capillaries, and are uncorrected. Powder diffraction spectra were obtained from a SCINTAG PAD V diffraction meter andmonochromatized CuK alpha radiation. GCMS data was collected from a 5890 Series II gas Chromatograph and HP 5971 mass selective detector. IR spectra were taken by diffuse reflectance in KBr using a Perkin Elmer 1720X FTIR at 4 cm$^{-1}$ resolution from 4000–450 cm$^{-1}$. NMR spectra were recorded on a Varian XL 200 MHz NMR at 24.5° C. Elemental analysis were preformed by Quantitative Technologies, Inc. (Salem, N.J.).

EXAMPLE A

SELENOL INTERMEDIATE

Sodium borohydride (2.1 g, 55.5 mmol) was added to a solution of selenium (4.0 g, 50.7 mmol) in a mixture of anhydrous ethanol and anhydrous chloroform (75 mL: 25 mL) at 0° C. under a nitrogen atmosphere. After 30 minutes the solution was brought to room temperature, and after an additional 30 minutes, the colorless solution was evaporated to dryness under vacuum to give a white powder (NaHSe). Ammonium chloride (0.5 g, 9.3 mmol), 2-bromopydridine (4.83 mL, 8.0 g, 50.7 mmol) and anhydrous dimenthylformide (100 mL) were added and the mixture was heated to 85° C. in the dark for 15 hours. The solvent was removed under vacuum and the yellow powder was washed first with cool water (100 mL) and then with a cool mixture of hexane and methanol (150 mL: 50 mL). The solid was dissolved in CH$_2$CL$_2$ (75 mL), the solution was filtered and cooled (−20° C.) to give yellow crystals of 2-Selenopyridine (4.5 g, 56.2%) that were identified by m.p (132° C.) and $^1$H NMR (CDCl$_3$): 8.41(1 H, broad), 7.86 (IH,d), 7.71 (1 H,d), 7.38 (IH,t) and 6.98 (IH, t).

EXAMPLE B

DISELENIDE INTERMEDIATES (1) Air was bubbled through a solution of 2-Selenopyridine (2g, 12.6 mmol) in water (100 ml) for 12 hours, and 2,2'-dipyridyl diselenide was separated by filtration, washed with a small amount of water and dried. The product was recrystallized from petroleum ether to give yellow needles; 1.5 g (78%), mp.47.9C.

(2) The product mixture from the preparation of 2-Selenopyridine was dissolved in DMF, cooled and then poured into 300 mL water and saturated with air bubbles for 12 hours. The solution was extracted with $CH_2Cl_2$(100 mL,50 mL,25 mL) and the solvent was removed under reduced pressure. The residual yellow powder was recrystallized from petroleum ether to give yellow needle like crystals.

EXAMPLE C

SYNTHESIS OF Di(3-TRIMETHYLSILYL-2-PYRIDYL) DISELENIDE

BuLi-TMEDA was found to be the most effective reagent for the ortho-lithiation of 2-pyridineselenol. A mixture of TMEDA (7 mL, 46.4 mmol) and pyridine-2-selenol (2.87 g, 18.2 mmol) in hexane (30 mL) was cooled to −78° C. and then treated dropwise with n-butyllithium (15.9 mL of a 2.5M solution in hexane, 39.8 mmol) in hexane. The temperature was kept constant for an hour and then raised to room temperature over a 3 hour period. The solution, which turned homogeneous, was stirred at RT for 12 hours, during which time an off-white solid formed.

The mixture was cooled to −78° C. and $Me_3SiCl$ (5.06 mL, 39.8 mmol) in THF (15 mL) was added slowly. After stirring at room temperature for 12 hours, the mixture was taken to dryness under vacuum. A solution of acetic acid (5 mL) in water (2L) was added to the solid and the product extracted with $CH_2Cl_2$(3×50 mL). The $CH_2Cl_2$extract was dried over $MgSO_4$, the solution was filtered and concentrated in a vacuum to give a yellow powder that was washed repeatedly with petroleum ether. (1.9 g 45%; m.p 202°–4° C.). Anal. Calcd for $CaH_{12}NSeSi$: C, 41.9;H,5.28;N,6.11. Found: C,41.3; H, 5.59; N, 5.97. ELMS: 460.0 (M+). 1H NMR ($CDCl_3$: 8.20 (IH.b), 7.59 (IH.d of d(J=7 Hz, 2 Hz)), 7.00 (1 H, broad t (J=6Hz)). IR (KBr): 3132 (m), 3100 (m), 3071 (m), 3036(s), 2965(s), 2919(s), 2892(s), 2849(s), 2757 (m), 2675(w), 1909(w), 1834(w), 1775(w), 1600(s), 1571 (s), 1545(m), 1478(w), 1428(w), 1356(m), 1303(s), 1245 (m), 1235(m), 1202(m), 1120(s), 1061(m), 1036(m), 1004 (w), 948(w), 897(w), 848(s), 749(s), 714(w), 697(m), 645 (m), 622(m), 416(m)cm$^4$.

EXAMPLE 1

SYNTHESIS OF $[Sn(2-SeNC_5H_4)_2]_2$

Method A

Pyridine-2-selenol (3.5 g, 22.2 mmol) was dissolved in THF (100 mL) to give an orange solution. After cooling the solution in an ice-water bath, $NaB(C_2H_5)_3H$ (22.3 mL of a 1M solution in THF, 22.3 mmol) was added and the solution turned pale yellow within 2 hours. The solvent was removed under vacuum to give a pale yellow powder (NaSePy) that was washed with diethyl ether. The powder was then added to a solution of $SnCl_2$ (2.1 g, 11.1 mmol) in THF (200 mL) and the mixture was stirred at room temperature for one day as a brown solution color developed. The solution was filtered, concentrated (75 mL) and layered with hexane (50 mL) to give yellow crystals (1.27 g, 26.4%; mp 114.6° C.).

Method B

Sn powder (0.5 g, 4.2 mmol) was mixed with dipyridyl diselenide (1.0 g, 3.2 mmol) in toluene (10 mL) and the mixture was then refluxed for 12 hours. The toluene was removed by vacuum to give a yellow powder that was first washed with diethyl ether (5×20mL) and then dissolved in THF (50 mL). Filtration, followed with saturation of the solution by layering with hexane, and gave yellow crystals (0.86 g, 62%) that were identical to the material isolated by method A.

Anal.Calced for $SnC_{10}H_8N_2Se_2$:C, 27.6; H,1.86; N,6.47. Found: C, 27.6; H,1.79; N,6.36. $^1$H NMR ($CD_3COCD_3$): 8.28 (1 H, d(J=5Hz)), 7.55(1H,m), 7.34(1 H, d(J=8Hz), 7.16(1H, t(J=6Hz)). The compound sublimes without decomposition at 107° C. ELMS: 435.8 (M+). IR (KBr): 1575 (s),1545(s), 1474 (w), 1441 (s),1410(s) 1262(s), 1235 (w), 1142(m), 1113(s), 1074(m), 1045(m), 1007(s)988(m), 872(w), 803(m),766(s),751(s), 730(w), 697(s), 639(m),624 (m), cm$^{-1}$.

EXAMPLE 2

SYNTHESIS OF $Sn(2-SeNC_5H_4)_4$

Dipyridyl diselenide (0.50 g, 1.59 mmol) and Sn (0.09 g,0.80 mmol) were mixed in toluene (10 mL). The mixture was stirred in the dark for 20 hours at 70° C. to give a yellow precipitate that was collected and washed with diethyl ether (50 mL). The product was redissolved in hot pyridine, the solution was filtered, and the pyridine was removed under vacuum to give a yellow powder (0.46 g, 77%; m.p 146–8). The product sublimes at 142° C. (0.1 mm Hg). Anal.Calcd for $C_{20}H_{18}N_4Se_4Sn$: C, 32.2; H, 2.16; N, 7.50. Found: C, 31.9; H, 2.10; N, 7.30. $^1$H NMR (DMSO): 8.11 (1H, d(J=5Hz)), 7.60(1H,m),7.51(1H,m), 7.17(1H,t(J=5 Hz)). IR (KBr: 1574 (s), 1562(s), 1555(s), 1468(w), 1435(s), 1417(s), 1358(m), 1272(w), 1257(s), 1241(m), 1149(s), 1119(s), 1102 (s), 1077(s), 1036(s), 1005(s), 985(s), 957(w), 883(w), 873 (w), 767(s), 750(s), 24(m), 696(s), 641(s), 616(m), 468(s), 415(s), 405(s)cm$^{-1}$.

EXAMPLE 3

SYNTHESIS OF $Pb(2-SeNC_5H_4)_2$

Method A $NaSeNC_5H_4$ (0.64 g, 3.55 mmol), prepared as above, was mixed with $PbCl_2$ (0.49 g, 1.78 mmol) in THF (100mL), and a green precipitate formed instantly. After one day, the solvent was removed under vacuum, to give a green powder (0.68 g, 63%). Alternatively, Pb(0.50 g, 2.41 mmol) was added to dipyridyl diselenide (0.76g, 2.42 mmol) in toluene (10 mL) and the mixture was refluxed for 12 hours. The solvent was removed by vacuum and the remaining powder was washed with diethyl ether (5×20 mL) and cold pyridine (5×20 mL). The product was then dissolved in hot pyridine, the mixture was filtered, and dried in vacuum to give a yellow-green powder (1.1 g, 88%; mp 230°–2° C.(dec)). Anal.Calcd for $C_{10}HBN_2PbSe_2$: C,23.0;H, 1.54; N,5.37 Found: C 22.6; H, 1.40; N, 5.01. The compound sublimes at 188° C. (0.1 mm Hg). ELMS: 523.9 (M+). $^1$H NMR (DMSO): 8.34 (1 H,d (J=4.4 Hz)), 7.41 (1 H, t (J=6.8 Hz)), 7.11 (2H, m). IR (KBr): 1570(s), 1546(m), 1440(s), 1407(s), 1263(m), 1228(w), 1144(m), 1108(s), 1071(m), 1040(m), 990(s), 755(s), 738(s), 697(s), 625(s), 471(s), 421(w), 405 (m)cm$^{-1}$.

Method B

NaSePy (1.13 g, 6.33 mmol) and lead (IV) tetraacetate (0.70 g, 1.58 mmol) were dissolved in THF (50 mL) and the mixture was stirred for 12 hours at room temperature. The solution was filtered, and the precipitate was washed with THF, MeOH, and $H_2O$ (5×30mL each) to give yellow $Pb(SePy)_2$ (0.5 g, 84%) and PySeSePy (0.41 g, 82%) that were identified by melting point and $^1$H-NMR spectroscopy. The organic product of the reaction was identified as di-pyridyl diselenide by passing the filtrate through a silica column before analysis by GCMS.

EXAMPLE 4

SYNTHESIS OF Pb(3-Me$_3$Si-2-SeNC$_5$H$_3$)$_2$

A solution of NaB(C$_2$H$_5$)$_3$H in THF (4.42 mL of a 1M solution, 4.42 mmol) was added to Di{3-trimethylsilyl-2-pyridine} diselenide (1.0 g,2.2 mmol) in THF (30 mL). After stirring the solution for two hours at room temperature, the solvent was removed under vacuum, and the resulting pale yellow solid was washed with diethyl ether (100 mL). The product was redissolved in THF, which was then removed by slow evaporation to give yellow crystals (0.76 g, 38.6%; mp 210°–2° C.) that were collected and washed with cold hexane. Anal.Calcd for PbC$_{16}$H$_{24}$N$_2$Se$_2$Si$_2$: C, 28.9; H, 3.63; N, 4.21. Found: C, 28.8; H, 3.36; N, 4.20. The compound sublimes at 145° C. (0.1 mm Hg) without decomposing. ELMS: 668.0 (M+). $^1$H NMR (CDCl$_3$): 8.41 (1 H, d of d (J=4.8 & 1.8 Hz)), 7.60 (1H,d of d (J=7.3 and 1.8 Hz)), 0.41 (9H, s). IR(KBr): 3094 (m), 3026(s), 2950(s), 2892(s), 1928(m), 1903(w), 1752(w), 1726(w), 1549(s), 1443 (w), 1407(m), 1354(s), 1245(s), 1223(m), 1200(m), 1119(s), 1057(s), 966(w), 942(w), 841(s), 786(m), 754(s), 687(s), 650(s), 622(s), 497(m), 439(m)cm-1. Unit cell (M$_o$K alpha radiation): a, 23.798(2) angstroms; b, 14.447(3) angstroms; c, 20.396(3) angstroms.

While only a few embodiments of the invention have been shown and described herein, it will become apparent to those skilled in the art that various modifications and changes can be made in the process to produce a stable single precursor compound having two or more metal atoms useful to produce metal alloys having a defined metal atom ratio and the precursors thereof without departing from the spirit and scope of the present invention. All such modifications and changes coming within the scope of the appended claims are intended to be carried out thereby.

We claim:

1. A single source metalloorganic 14–16 semiconductor precursor compound of the formula:

(2-NR-Q-)$_l$M-A$_m$ (l=0–4, m=0–4, l+m=2 or 4)

wherein M is selected from the Group 14 elements of germanium, tin or lead;

A is selected from amide, alkyl having from 1 to 20 carbon atoms, aryl, substituted aryl, or Q'-2-NR'L$_n$ (n=1–4) wherein L is selected from nothing or a Lewis base ligand;

Q and Q' selenium; and

2-NR and 2-NR' are each independently selected from N-heterocyclic aryl or its derivatives.

2. The metal compound of claim 1 wherein A is -Q-2-NR' and L is nothing.

3. The metal compound of claim 2 wherein 2-NR=2-NR' and Q=Q'.

4. The metal compound of claim 3 wherein 2-NR= pyridinyl or 3-TMS-2-pyridinyl.

5. The metal compound of claim 1 wherein M is Germanium.

6. The metal compound of claim 1 wherein M is Tin.

7. The metal compound of claim 1 wherein M is Lead.

8. The claim metal compound of claim 1 wherein 2-NR= substituted 2-pyridinyl.

9. The metal compound of claim 1 wherein L, the Lewis base ligand, is present and is independently selected from pyridine, substituted pyridine, pyrrole, substituted pyrrole, quinoline, morpholine, 2,2'bipyridyl, organic phosphine, organic arsine, alkyl, ether, aryl ether, thioether, amine, chelate of diamines, diphosphines, diarsines, diethers, or mixtures thereof.

10. The metal organic compound of claim 1 wherein L, the Lewis base ligand, is present and is independently selected from pyridine, substituted pyridine, pyrrole, substituted pyrrole, quinoline, morpholine, 2,2' bipyridyl, organic phosphine, organic arsine, alkyl ether, aryl ether, thioether, amine, chelate of diamines, diphosphines, diarsines, diethers or mixtures thereof.

11. The metal compound of claim 10 wherein M is Germanium.

12. The metal compound of claim 10 wherein M is Tin.

13. The metal compound of claim 10 wherein M is Lead.

14. A process for the production of a single source metalloorganic 14–16 semiconductor precursor compound for the formula:

(2-NR-Q-)$_l$M-A$_m$ wherein M is selected from the Group 14 elements of germanium, tin or lead;

A is selected from an amide, an alkyl having from 1 to 20 carbon atoms, an aryl, a substituted anyl, or -Q'2-NR'L$_n$ (n=1–4) wherein L is nothing or a Lewis base ligand, Q and Q' are each independently selected for Group VIa elements of of sulfur, selenium or tellurium and 2-NR and 2-NR' are each independently selected from N-heterocyclic aryl or its derivatives, which process comprises:

(A) contacting L'$_n$-Z-2-NR (n=1–4) wherein L' is independently selected from ligand L, Z is independently selected from lithium, sodium, potassium, calcium, barium, or strontium; and 2-NR is defined as hereinabove, with a metal powder Q wherein Q is defined hereinabove, in a hydrocarbon solvent under an inert anhydrous atmosphere for between about 0.01 and 2 hours at between about −20° and +30° C.;

(B) contacting the product of step (A) with an acid, and removing the polar solvent to give

H-Q-2-NR wherein Q and 2-NR are defined hereinabove;

(C) contacting the product of step (B) with:

(1)MX$_n$ (n=2 or 4) salt in a n:1 ratio in organic solvent at between −20° and +30° C., and for between about 0.01 and 2 hours, or (2)MR$_n$ (n=2 or 4) in a n: 1 ratio in a polar solvent at between −20° and +30° C., and for between about 0.01 and 2 hours, or (3)M(R')$_n$ or MX$_n$ (n=2 or 4) wherein R' is independently selected from R and R is defined as an alkyl, aryl, substituted aryl, amino beta-diketonate, in any ratio in a polar solvent at between −20° and +100 ° C. and for between about 0.01 and 2 hours, followed by treatment with one H-Q'-2-NR', where Q' and 2-NR' are defined above, in a polar solvent at between −20° and +100° C. and for between about 0.01 and 2 hours;

(D) recovering the metalloorganic compound of structure (I), where L is nothing; and (E) optionally contacting the product of step (D) with ligand L to produce an organometallic compound where L is a Lewis base.

15. A process for the production of a di-, tri-, or tetrametal alloy, which process comprises:

(F) subjecting the metalloorganic compound step (D) or step (E) of claim 16 to a temperature of between about 150° and 500° C. in an anhydrous vacuum between about ambient pressure to 10$^{-6}$ Torr.

16. The process of claim 14 wherein A is -Q-2-NR' and 2-NR'=2-NR', Q=Q', and L is nothing.

* * * * *